United States Patent [19]

Bull

[11] Patent Number: 5,098,186
[45] Date of Patent: Mar. 24, 1992

[54] STOPPED FLOW SPECTROPHOTOMETER MIXER

[76] Inventor: Christopher Bull, 5525 Charles, Bethesda, Md. 20814

[21] Appl. No.: 596,711

[22] Filed: Oct. 12, 1990

[51] Int. Cl.⁵ ............................................. G01N 21/05
[52] U.S. Cl. ........................................................ 356/246
[58] Field of Search .................................. 356/244, 246

[56] References Cited

U.S. PATENT DOCUMENTS

| | | |
|---|---|---|
| 515,618 | 2/1894 | Saladin . |
| 3,815,789 | 6/1974 | Carpigiani . |
| 3,932,136 | 1/1976 | Stickney . |
| 3,970,388 | 7/1976 | Hacker ............................ 356/246 X |
| 4,076,420 | 2/1978 | De Maeyer et al. ................. 356/73 |
| 4,399,101 | 8/1983 | Queen .................................. 422/68 |

*Primary Examiner*—Vincent P. McGraw
*Attorney, Agent, or Firm*—William S. Ramsey

[57] ABSTRACT

An improvement in rapid mixers for stopped flow spectrophotometers is disclosed. This improvement involves the dispersion of one solution from the bore of a disperser through notches into a flowing sheath of a second solution. The dispersed mixture is then mixed by passage through a mixer made up of a series of mixing rings with lands and grooves. The lands and grooves of adjoining rings are aligned so grooves are adjacent to lands, thus providing maximum mixing. The ratio of volumes of solutions mixed may vary from 1:1 to 40:1 by varying the number and size of notches in the end of the disperser tube. The viscosity ratio of the solutions mixed may vary from 1:1 to 100:1. Complete (greater than 99%) mixing occurs in less than one millisecond.

11 Claims, 3 Drawing Sheets

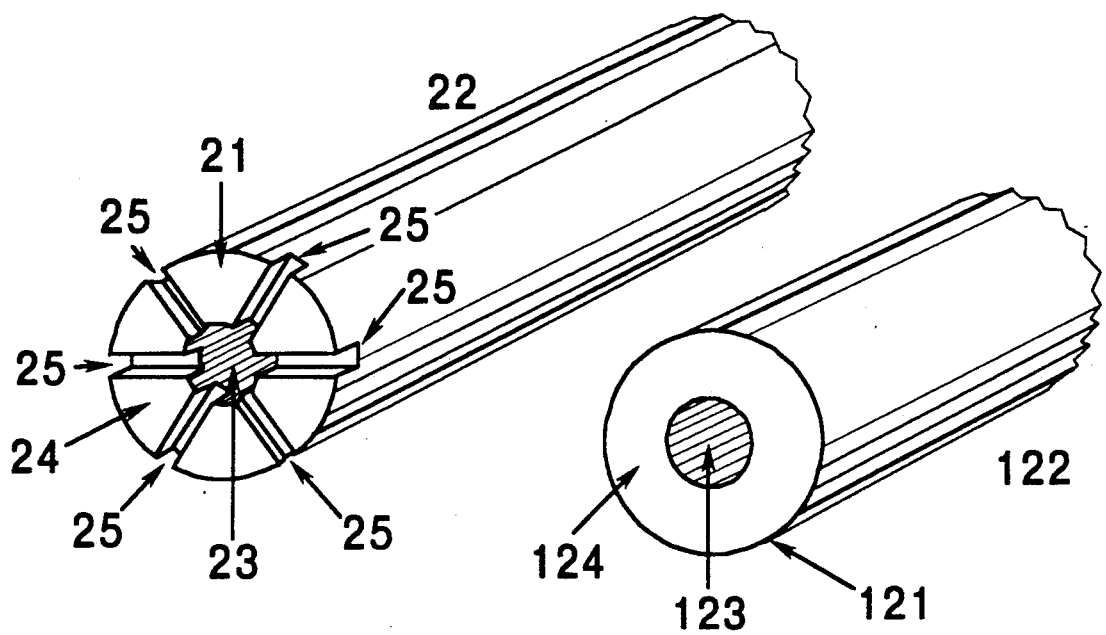
Figure 3
Figure 4
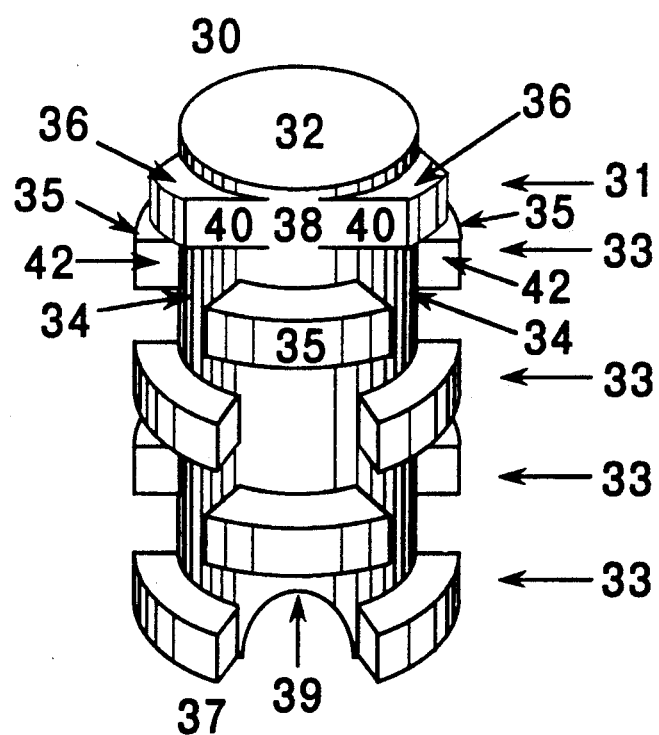
Figure 5

STOPPED FLOW SPECTROPHOTOMETER MIXER

BACKGROUND OF THE INVENTION

1. Field of the Invention

This invention relates to fluid testing and evaluating apparatus for evaluating mixtures of fluids, usually liquids, under static conditions.

2. Description of Related Art

The stopped flow method, particularly as applied to spectroscopy, is the most commonly used technique for observation and characterization of intermediates involved in chemical reactions. This method involves the mixing of two or more chemical reagents together within 1 or 2 milliseconds (msec) and placing them into a suitable observation chamber, where measurement may be made until the reaction is complete. The total range in time can be seconds, minutes, or hours as required.

A number of mixers for use with stopped flow spectroscopy appear in the U.S. Patent records. U.S. Pat. No. 3,932,136 describes a ball mixer in which two chemical reactants are directed to the surface of a hemisphere where they are mixed. U.S. Pat. No. 3,970,388 describes a mixing element provided with annular grooves and axially extending passages interconnecting the annular grooves. U.S. Pat. No. 4,076,420 describes a mixer in which mixing occurs in two counterrotating vortexes. U.S. Pat. No. 4,399,101 describes a mixing chamber which two legs of a bifurcated bore meet in a meeting point which constitutes a first mixing point. A second mixing point occurs in a short bore extending to a light point bore. This involves two t-type mixers.

The present invention has properties not found in the prior art; it mixes thoroughly (greater than 99%) in less than 1 msec, it mixes reactants in a volumetric ratio up to 40:1, and it mixes reactants of widely different viscosities, up to a ratio of 100:1.

SUMMARY OF THE INVENTION

The mixer of the present invention may be thought of as having a dispersing zone followed by a mixing zone. A chemical reactant solution (CRS) is pumped through a cylindrical dispersion tube. The flow impinges on a flat mixing post and is dispersed radially through radial notches. The radial flow is dispersed into a flowing sheath of the second CRS which is flowing along the outer surface of the dispersion tube. The dispersed solutions immediately enter the mixer which is a series of rings having aligned grooves and lands forming a labyrinth which thoroughly and quickly mixes the solutions. The volumetric ratios of solutions mixed may be altered accurately and conveniently by substituting disperser tubes varying in the number and size of radial notches. In addition, CRSs varying greatly in viscosities may be mixed using a disperser tube with a suitable array of radial notches. A second embodiment is disclosed in which the disperser tube has no notches on the flattened end and is biased against the mixing post by a resilient gasket. In this embodiment, hydraulic pressure inside the disperser tube bore forces the tube to move against the resilient bias allowing the fluid inside the disperser tube to be dispersed into the flowing sheath of fluid.

It is an object of the invention to provide a mixer which achieves thorough (greater than 99%) mixing in less than 1 msec.

It is another object of the invention to provide a mixer which may be used to mix varying volumes of CRSs up to a ratio of 100:1.

It is another object of the invention to provide a mixer in which the volumes of CRSs mixed may be accurately and easily varied.

It is another object of the invention to provide a mixer in which the disperser tube may be easily changed.

It is another object of the invention to provide a mixer which may be used to mix CRSs of varying viscosities up to a ratio of 100:1.

It is another object of the invention to provide a mixer in which the dispersion and mixer elements are always oriented to provide optimum mixing.

It is another object of the invention to provide a mixer which is easily and inexpensively fabricated.

BRIEF DESCRIPTION OF THE DRAWINGS

FIG. 3 is a perspective view of the disperser tube embodiment 1.

FIG. 4 is a perspective view of the disperser tube embodiment 2.

FIG. 5 is a perspective view of the mixer post.

DESCRIPTION OF THE PREFERRED EMBODIMENTS

Figure 1:
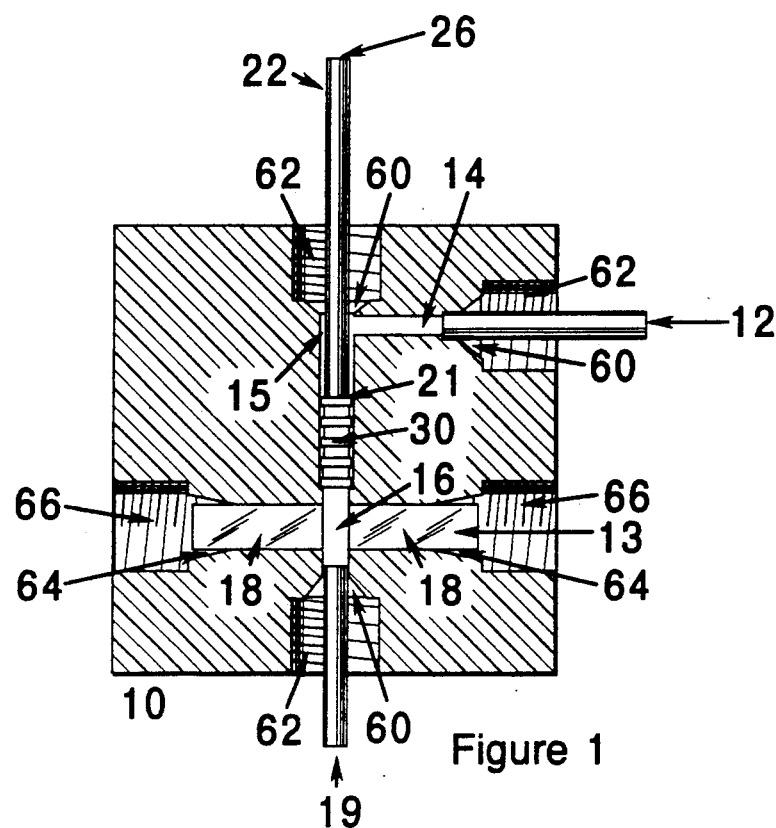
FIG. 1 is a diagrammatical cross-section view of the mixer block showing the mixer elements in perspective.

FIG. 1 is a partial cross section view which shows the mixer block incorporating this invention. In FIG. 1 the disperser tube, feed tube, mixer post, and drainage tube are shown in perspective. In the preferred embodiment the mixer block is mounted in a stopped flow spectrophotometer manufactured by Kinetic Instruments, Inc., Ann Arbor, MI, (not shown) although the mixer block may be used with any suitable stopped flow spectrophotometer. The mixer block is secured in the spectrophotometer by bolts, screws, flanges, or other suitable fastening devices (not shown). Two cylindrical cavities, 13 and 15 are bored through adjacent sides of the mixer block and intersected forming an observational chamber 16. Cylindrical cavity 15 contains the mixer elements, disperser tube 26 and mixer post 30. The observational chamber 16 is drained by drainage tube 19. Cylindrical cavity 13 contains quartz lenses 18. A filling port 14 intersects cavity 15 above the mixer post. Feed tube 12 fills port 14 with one CRS which fills the annular space 20, FIG. 2 between the cylindrical cavity wall 11, FIG. 2 and the disperser tube. The first CRS forms a sheath around the disperser tube and flows toward the mixer post 30. The second CRS is provided through the bore at the second end 26 of disperser tube 22. The second CRS flows through the disperser tube to the first end 21 of the disperser tube where it is dispersed into the flowing sheath of second CRS. The disperser and feed tubes are connected by tubes to conventional syringes (not shown) which deliver the CRSs when activated. The reacted CRSs are drained from the mixing block through drainage tube 19. The reacted CRSs then activate the stopping syringe (not shown).

The disperser tube 22, feed tube 12, and drainage tube 19 are held in position and sealed against leakage by resilient toroid-shaped ferrules, gaskets or grommets 60. The ferrules are secured in place by apertured threaded nuts or plugs 62 which mesh with corresponding threads in the mixer block. The disperser tube 22, feed tube 12, and drainage tube 19 pass through the apertures in the nuts 62. Quartz windows 18 are inserted in cylindrical cavity 13 and are held in place by resilient toroid-shaped ferrules, gaskets or grommets 64. The ferrules are secured in place by apertured threaded nuts or plugs 66 which mesh with corresponding threads in the mixer block. Light used in observations passes through cavity 13.

Figure 2:
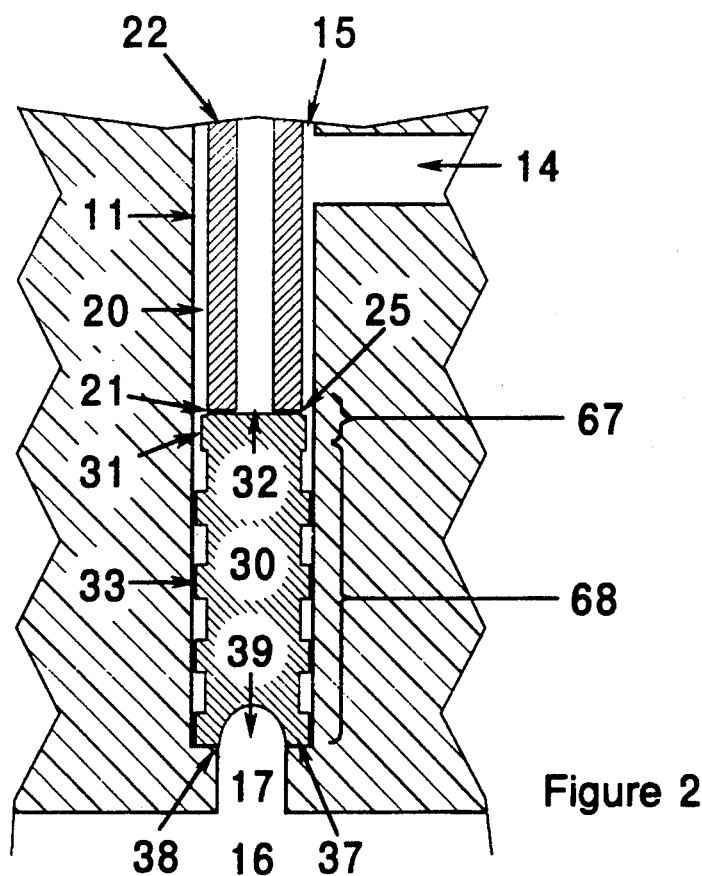
FIG. 2 is a diagrammatical cross-section view of the mixer elements mounted in a mixer block.

FIG. 2 is a cross section view of a portion of the mixer block showing the mounting of the disperser tube 22 and mixer post 30. The first cylindrical cavity 15 has a cavity wall 11. The diameter of cylindrical cavity 15 is greater than the diameter of the disperser tube 22, forming an annular cavity 20 which surrounds the disperser tube, which is mounted in the center of the cylindrical cavity. Port 14 delivers a first CRS to the annular cavity 20. The cylindrical cavity 15 has a shoulder 38 which supports the second end 37 of the mixer post 30. The mixer post 30 has a series of rings 31, 33 which extend from the mixer post 30 to the cavity wall 11. The mixer post 30 and disperser tube 22 are mounted coaxially in the cylindrical cavity, with the center of the bore of the disperser tube aligned with the center of the cross-section of the mixer post. The mixer post is supported in the cylindrical cavity by a shoulder 38 in the cavity wall 11. The second end 37 of the mixer post 30 rests on the shoulder 38. The first end 21 of the disperser tube 22 abuts the first end 32 of the mixer post 30. The flat wall portion of the first embodiment disperser tube 24, FIG. 2, or of the second embodiment disperser tube 124, FIG. 3 is juxtaposed against the flat first end 32 of the mixer post 30. Thus a CRS in the first embodiment disperser tube is dispersed into the annular cavity through the grooves 25. A CRS in the second embodiment disperser tube is dispersed into the annular cavity through displacement of the disperser tube away from the mixer post.

FIG. 3 is a perspective view of a portion of the first embodiment disperser tube 22 showing the first end 21. A bore 23 is located in the center of the disperser tube 22. At a first end 21 the tube wall 24 is flat and the wall surface is perpendicular to the long axis of the tube. The long axis of the tube extends from the first to the second end of the tube. The tube wall 24 has 6 radial notches, cuts or grooves 25 which extend radially across the flat tube wall 24 from the bore 23 to the outer surface of the disperser tube. In this preferred embodiment the notches 25 are square in cross-section but they may be V-shaped, hemispherical, or of any other suitable shape. In one preferred example the notches are 20/1000 inches in depth and width. This disperser is used when approximately equal volumes of CSRs are to be mixed. In another preferred example the notches are 3/1000 inches in depth and width. This disperser is used when a volumetric ratio of a first to a second CSR of 40:1 is desired. One disperser tube may be replaced by another disperser tube having more or fewer notches, or notches of a different shape or size, depending on the nature of CRSs under study and the desired volumetric ratio of one CRS being mixed to another. In operation, a second CRS is delivered from a syringe to the second end 26, flows down the bore of the disperser tube, impinges on the top 32, FIG. 4 of the mixer post 30, flows radially outward through the notches 25, and is dispersed into the sheath of first CRS which flows along the outside of the disperser tube.

FIG. 4 is a perspective view of a portion of a second embodiment disperser tube 122 showing the first end 121. In this embodiment disperser tube 122 has a bore 123 and a first end 121. At the first end 121 the tube wall 124 is flat and the wall surface is perpendicular to the long axis of the disperser tube. The second embodiment disperser tube is secured to the mixer block and a CRS is fed into a second end of the disperser tube as in the disperser tube first embodiment. The flat end 124 of the disperser tube second embodiment interacts with the first end 32, FIG. 4 of mixer post 30 to seal the bore of the disperser tube second embodiment. In operation, hydraulic pressure of a second CRS within the disperser tube overcomes the spring bias of the ferrule sealing the tube in place and displaces the disperser tube toward the ferrule. This displacement of the disperser tube allows the second CRS to disperse evenly from the circumference of the disperser tube end into the sheath of first CRS which flows along the outside of the disperser tube.

FIG. 5 shows a perspective view of a mixer post 30 having a first 32 and second end 37. The long axis of the mixer post extends from the first to the second end. The first end 32 of the mixer post has a flat surface which is perpendicular to the long axis of the mixer post. The first end 32 bears against and abuts the first end 21 of the disperser tube forming a dispersing zone 67 FIG. 2 in the annular space 20 FIG. 2. The dispersing zone is the region of the annular space where a second CRS is dispersed into the flowing sheath of first CRS.

A first annular ring 31 FIG. 5 is located below the first end 32 of the mixer post. Four additional annular rings 33 are equidistantly arrayed along the length of the mixer post. Each annular ring extends from the mixer post to the cavity wall 11. From 1 to 9 additional annular rings may be used. The rings form a mixing zone 68 FIG. 2. The mixing zone is the region of the annular space where the mixer post rings partially fill the annular space and extends from the first to the last mixer post ring. The dispersed CRSs are mixed in the mixing zone. The first annular ring 31 has 3 openings which transverse the ring with the formation of 3 grooves 38 and 3 lands 36 of uninterrupted annular ring material. The land walls 40 of a first ring land 36 are located approximately on a tangent to the mixer post surface. The walls 40 of two adjacent lands 36 lie on a plane. Each additional annular ring 33 has 3 openings which transverse the ring with the formation of 3 grooves 34 and 3 lands 35 of uninturrupted annular ring material. The land wall 42 of an additional ring land 35 lies perpendicular to a tangent to the mixer post surface. The grooves permit passage of liquid from one side of the ring to the other. The grooves are distributed symmetrically and equidistance from each other around the circumference of a ring. From 2 to 6 grooves may be used. In this preferred embodiment the ratio of number of notches on the first embodiment disperser tube to number of grooves on the first annular ring nearest the disperser tube is 2 to 1. This insures that the same thorough mixing will be accomplished regardless of the orientation of the disperser tube about its long axis with respect to the mixer post. The grooves are arranged so that a groove on one annular ring is adjacent to the middle of a land on an adjoining or adjacent annular ring. Fluid passing through the mixing zone will transverse a labyrinth of grooves and lands thereby assuring thorough mixing.

Figure 7:
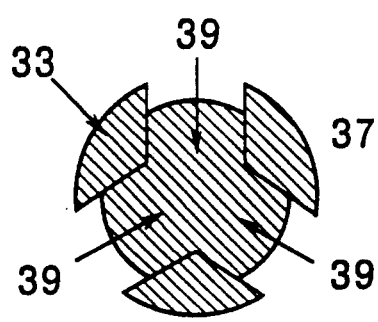
FIG. 7 is a bottom view bottom of the mixer post.

At the second end 37 of the mixing post 30 a hemispherical cut 39 is made from the outer surface to the center of the mixer post at each groove in the annular ring. These cuts allow the mixed CRSs to flow into the mixer duct 17 FIG. 2 which leads to the observational chamber 16 FIG. 2. FIG. 7 is a bottom view of the second end of the mixer post showing the hemispherical cuts 39 and ring 33 at the end of the mixer tube.

Figure 6:
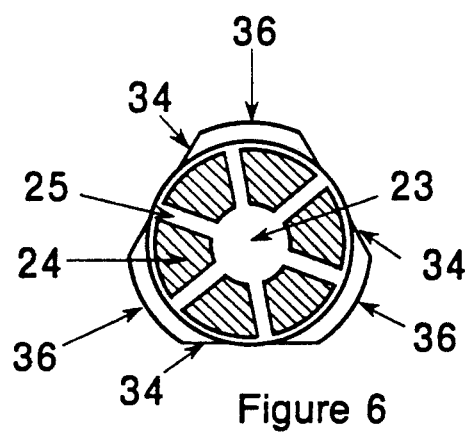
FIG. 6 is a top view of the mixer post with the notches of the disperser tube superimposed to show orientation.

FIG. 6 is a diagrammatic view showing the relationship between the first embodiment disperser tube and the first ring on the mixer tube. This view shows the lands 36 and grooves 34 of the first ring on the mixer post, and the bore 23 of the first embodiment disperser tube, the flat wall of the first end 24 of the disperser tube, and the notches 25 which axially transverse the flat wall. Every axial orientation of the mixer post and first embodiment disperser tube results in the same number of notches aligned with grooves. The flow into each groove on the mixer post stems from the same number of notches on the disperser tube. This relationship results from the 2:1 ratio of numbers of notches on the disperser tube to number of grooves on the first ring on the mixing post.

The mixer block and ferrules are constructed of "KEL-F" polychlorotrifluoroethylene resin. "KEL-F" is a trademark for a polychlorotrifluoroethylene resin sold by 3M Products, St. Paul, MN. The mixer post is made of titanium. The disperser, feed, and drain tubes are made of 316 stainless steel. Other suitable materials may be used.

In operation, the first and second syringe are loaded with a first and second CRS, respectively. On activation of the first syringe, a first CRS flows into and fills the annular space creating a sheath of first CRS which flows toward the mixer post. On simultaneous activation of the second syringe a second CRS fills the first embodiment disperser tube bore and flows through the notches into the dispersion zone and is dispersed into the sheath of first CRS flowing into the dispersion zone. In operation, a second CRS fills the second embodiment disperser tube bore. When the hydraulic pressure is adequate, the second embodiment dispersion tube is displaced away from the mixer post and the second CRS flows between the disperser tube wall and the mixer post into the sheath of first CRS flowing into the dispersion zone. The dispersed CRSs flow into the mixer zone and are thoroughly mixed by transversing the labyrinth of grooves and lands on the annular rings. The mixed CRSs flow through the hemispherical cuts into the mixer duct and into the observational cell. The mixed CSRs then flow from the observational cell into the drainage tube and into the stopper syringe.

EXAMPLES

Figure 8:
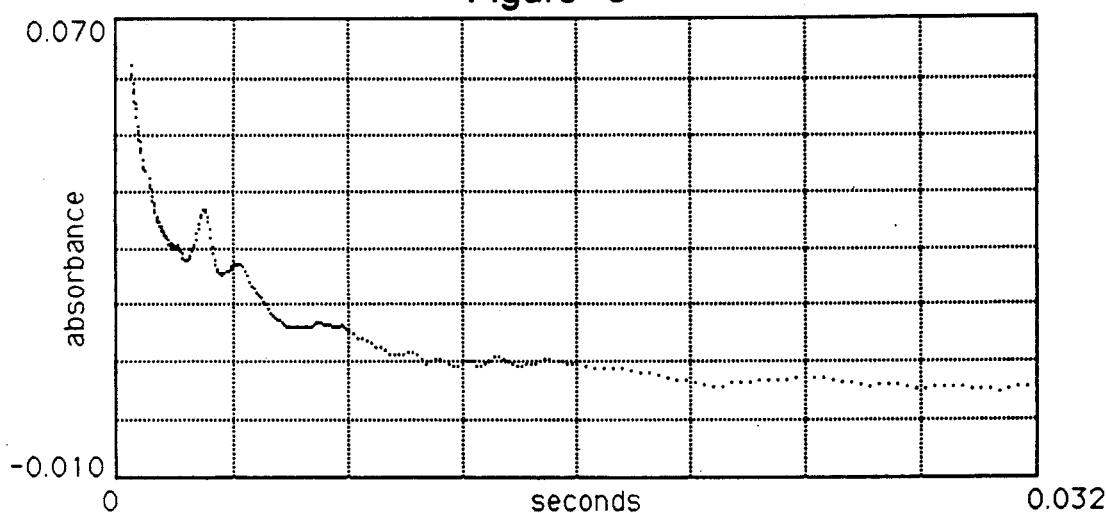
FIG. 8 shows mixing of glycerol and water using a conventional mixer.
Figure 9:
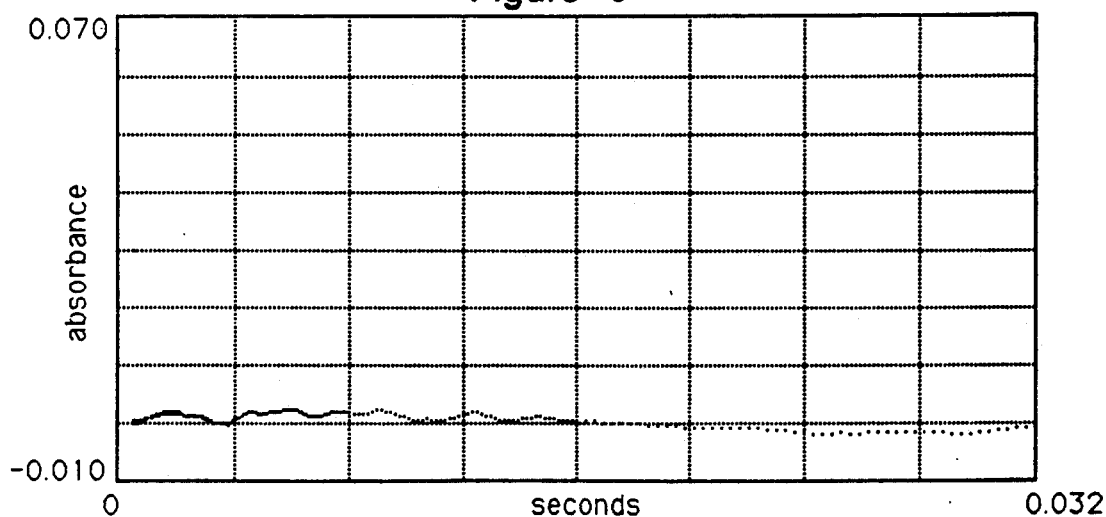
FIG. 9 shows mixing of glycerol and water using the mixer of this invention.

FIGS. 8 and 9 compared the use of a conventional mixer and the mixer of this invention. FIG. 8 showed the absorbance of a mixture of glycerol and water mixed using a t-type mixer in a stopped flow spectrophotometer manufactured by Kinetic Instruments, Inc., Ann Arbor MI. In this example, 1 part by volume 20% by volume glycerol in water was mixed with 1 part by volume water. In FIGS. 8 and 9 the abscissa was time in sec after stop of flow, the ordinant was absorbance measured at 534 nm. In this determination, absorbance can stem only from schlieren patterns from imperfect mixing of glycerol and water. FIG. 8 showed the mixing of glycerol and water achieved using a conventional t-type mixer. FIG. 9 showed the the results under the same conditions as FIG. 8 except the mixer block of the present invention was used. The absorbance in FIG. 9 was about flat within 1 msec after the stop of flow. This showed that the mixer of the present invention was superior in performance to the conventional mixer in mixing 20% by volume glycerol in water with water at a volumetic ratio of 1:1.

It will be appreciated that the basic mixer concept described above may be employed on many different styles and configurations of mixers without departing from the spirit or scope of the inventions.

I claim:

1. A mixer for a stopped flow spectrophotometer comprising:
   a mixer block having a dispersing zone for dispersing a second solution into a first solution,
   a labyrinth mixing zone for mixing dispersed first and second solutions, an observational chamber,
   means for delivering first and second solutions to the mixer block, and
   means for delivering mixed solutions to the observational chamber.

2. A mixer for a stopped flow spectrophotometer comprising:
   a mixer block penetrated by a cylindrical cavity having a cavity wall,
   a disperser tube having a first and a second end which is disposed in the cylindrical cavity,
   a mixer post having a first and second end which is disposed in the cylindrical cavity with the first end abutting the first end of the disperser tube and having rings consisting of lands and grooves arrayed around the mixer tube,
   an observational chamber,
   means for delivering a first solution to the cylindrical cavity,
   means for delivering a second solution to the disperser tube, and means for delivering mixed solutions to the observational chamber.

3. The mixer of claim 2 wherein the first end of the disperser tube has has a flat wall surface perpendicular to the long axis of the tube, and the surface is transversed by a plurality of notches extending radially across the flat wall surface.

4. The mixer of claim 2 wherein the disperser tube is biased against the mixer post by biasing means and the first end of the disperser tube has a flat wall surface perpendicular to the long axis of the tube which is smooth and free of notches or other voids.

5. The mixer of claim 2 wherein the number of rings on the mixer post is 2 to 10.

6. The mixer of claim 2 wherein the number of rings on the mixer post is 5.

7. The mixer of claim 2 wherein the disperser tube has a first end with a flat surface in which the number of notches and the number of grooves in each ring on the mixing post are in the ratio of 2 to 1.

8. The mixer of claim 2 wherein the disperser tube has a first end with 6 notches and the mixer post has rings with 3 grooves.

9. The mixer of claim 2 wherein the first and second solutions have volumes in ratios of 1:1 to 40:1.

10. The mixer of claim 2 wherein the first and second solutions have viscosities in the ratio of 1:1 to 100:1.

11. A mixer for a stopped flow spectrophotometer comprising:

a mixer block penetrated by a cylindrical cavity having a cavity wall, a cylindrical disperser tube having an outer diameter less than the diameter of the cylindrical cavity mounted by mounting means in the center of the cylindrical cavity, forming an annular space between the disperser tube and the cavity wall through which a first solution may flow as a sheath surrounding the dispersing tube, said dispenser tube having an axial bore, a first end having a flat wall surface perpendicular to the long axis of the tube, and a plurality of radial notches extending radially across the flat wall surface from the bore to the annular space and equidistantly arrayed about the circumferance of the disperser tube, a cylindrical mixing post having a first and a second end and a outer diameter less than the diameter of the mixing block cylindrical cavity and having a first end with a flat surface perpendicular to the long axis of the mixer tube, said mixing post mounted by mounting means coaxially with the disperser tube in the cylindrical cavity, the first end of the mixer post abutting the flat wall surface of the dispersing tube first end and forming hydraulic connection between the dispersing tube bore through the radial notches to the annular space and forming a dispersing zone in the annular space where a second solution from inside the bore may be dispersed through the notches into a first solution flowing as a sheath surrounding the dispersing tube, a plurality of annular rings filling the annular space between the mixer post and the mixer block cylindrical cavity wall, each ring penetrated by more than one groove with the formation of grooves and lands, said grooves and lands equidistantly distributed about each ring, said grooves and lands aligned so that each groove is adjacent to a land in an adjoining ring forming a mixing zone in which the dispersed solutions are mixed by being alternately separated and combined in a labyrinth, an observational chamber, fluid delivery means for delivering a first solution to the annular space surrounding the dispersing tube forming a sheath of first solution for dispersing with a second solution, fluid delivery means for delivering a second solution to the bore of the dispersing tube for transfer through the radial notches to the annular space for dispersing with a first solution, and means for delivering the solutions to the observational chamber.

* * * * *